United States Patent
Locke et al.

(10) Patent No.: US 9,125,767 B2
(45) Date of Patent: Sep. 8, 2015

(54) WOUND FILLER HAVING DYNAMIC MOTION

(71) Applicant: KCI Licensing, Inc., San Antonio, TX (US)

(72) Inventors: Christopher Brian Locke, Bournemouth (GB); James A. Luckemeyer, San Antonio, TX (US); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 341 days.

(21) Appl. No.: 13/714,119

(22) Filed: Dec. 13, 2012

(65) Prior Publication Data

US 2013/0165836 A1 Jun. 27, 2013

Related U.S. Application Data

(60) Provisional application No. 61/578,802, filed on Dec. 21, 2011.

(51) Int. Cl.
*A61F 13/00* (2006.01)
*A61L 15/42* (2006.01)

(52) U.S. Cl.
CPC ..... *A61F 13/00068* (2013.01); *A61F 13/00008* (2013.01); *A61L 15/42* (2013.01);
(Continued)

(58) Field of Classification Search
CPC ..... A61F 13/00; A61F 13/02; A61F 13/0203; A61F 2013/00548; A61F 2013/00238; A61F 2013/00919; A61F 2013/00174; A61F 2013/00536; A61F 13/00068; A61L 15/42; A61M 27/00

USPC ........ 602/48, 41–42, 2, 43, 52; 604/289, 290, 604/304–306, 313, 319
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

(Continued)

*Primary Examiner* — Kim M Lewis (57) ABSTRACT

Systems and apparatuses for administering reduced pressure treatment to a tissue site including a wound filler for positioning adjacent a wound site on a patient. The wound filler includes at least one strand having a plurality of nodes positioned along a length of the strand. The at least one strand has a charged state and an uncharged state. In the charged state, the at least one strand includes a stored energy that when released would deform or move the at least one strand. In the discharged state, the stored energy has been released. The wound filler further includes a removable sheath encasing the at least one strand. The at least one strand transitions from the charged state to the uncharged state as the removable sheath is removed.

40 Claims, 5 Drawing Sheets

(52) U.S. Cl.
CPC .................. *A61F2013/0028* (2013.01); *A61F 2013/00174* (2013.01); *A61F 2013/00238* (2013.01); *A61F 2013/00536* (2013.01); *A61F 2013/00548* (2013.01); *A61F 2013/00919* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,470,625 A * | 11/1995 | Perrault | 428/48 |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,833,642 A * | 11/1998 | McCabe et al. | 602/43 |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2008/0167593 A1 | 7/2008 | Fleischmann | |
| 2010/0160874 A1 | 6/2010 | Robinson et al. | |
| 2010/0160876 A1 | 6/2010 | Robinson et al. | |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | WO 99/64080 A1 | 12/1999 |
| WO | WO 01/23653 A1 | 5/2001 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

(56) References Cited

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ð ukić, Ž. Maksimović, Ð . Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
International Search Report and Written Opinion for corresponding PCT/US2012/069551, mailed Apr. 15, 2013.

* cited by examiner

WOUND FILLER HAVING DYNAMIC MOTION

CROSS-REFERENCE TO RELATED APPLICATION

This application claims priority to U.S. Provisional Patent Application No. 61/578,802 filed Dec. 21, 2011, entitled A WOUND FILLER HAVING DYNAMIC MOTION, the disclosure of which is hereby incorporated by reference in its entirety.

BACKGROUND

1. Field

The subject matter of this specification relates generally to reduced pressure treatment systems and more particularly, but not by way of limitation, to a wound filler having dynamic motion.

2. Description of Related Art

Clinical studies and practice have shown that providing a reduced pressure in proximity to a tissue site augments and accelerates the growth of new tissue at the tissue site The applications of this phenomenon are numerous, but one particular application of reduced pressure involves treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and micro-deformation of tissue at the wound site Together these benefits result in increased development of granulation tissue and faster healing times. Typically, reduced pressure is applied by a reduced pressure source to tissue through a porous pad or other manifold device. The porous pad contains cells or pores that are capable of distributing reduced pressure to the tissue and channeling fluids that are drawn from the tissue. The porous pad often is incorporated into a dressing having other components that facilitate treatment.

SUMMARY

The problems presented by existing reduced pressure treatment systems are solved by the systems and methods of the illustrative embodiments described herein. In one illustrative embodiment, a wound filler for positioning adjacent a wound site on a patient includes at least one strand having a plurality of nodes positioned along a length of the strand. The strand has a charged state and an uncharged state. In the charged state, the strand includes a stored energy that when released would deform or move the strand. In the discharged state, the stored energy has been released. The wound filler further includes a removable sheath encasing the strand. The strand can transition from the charged state to the uncharged state as the removable sheath is removed.

In another embodiment, a wound filler for positioning adjacent a wound site on a patient for treating the wound site with reduced pressure includes a first strand having a plurality of nodes positioned along a length of the first strand, a second strand having a plurality of nodes positioned along a length of the second strand, and rods connecting the first strand to the second strand. A dissolvable membrane surrounds the first strand and the second strand. The wound filler has a charged state in which the first and second strands include a stored energy that when released would deform or move the plurality of nodes on the first and second strands, and an uncharged state in which the stored energy has been released. The wound filler can transition from the charged state to the uncharged state as the membrane softens in the presence of wound fluid. The transition is configured to dynamically change the position of the plurality of nodes against the wound site.

In yet another embodiment, a wound filler for positioning adjacent a wound site on a patient for treating the wound site with reduced pressure includes a web having a plurality of nodes positioned on the web, and a removable membrane fitted around the web such that a shape of the plurality of nodes is visible. The membrane holds the web in a first, potential energy state that when released would deform or move the plurality of nodes. The web gradually transitions into a second, resting state as the membrane dissolves in the presence of wound fluid.

In another embodiment, a system for treating a wound site on a patient with reduced pressure includes a wound filler. The wound filler includes at least one strand having a plurality of nodes positioned along a length of the strand. The strand has a charged state and an uncharged state. In the charged state, the strand includes a stored energy that when released would deform or move the strand. In the discharged state, the stored energy has been released. The wound filler further includes a removable sheath encasing the strand. The strand transitions from the charged state to the uncharged state as the removable sheath is removed. The system further includes a drape positioned over the wound filler and capable of attaching to an intact portion of the patient's epidermis for creating a sealed space beneath the drape and a reduced pressure source for supplying reduced pressure to the sealed space.

In another embodiment, a system for treating a wound site on a patient with reduced pressure includes a wound filler. The wound filler includes a first strand having a plurality of nodes positioned along a length of the first strand, a second strand having a plurality of nodes positioned along a length of the second strand, and rods connecting the first strand to the second strand. A dissolvable membrane surrounds the first strand and the second strand. The wound filler has a charged state in which the first and second strands include a stored energy that when released would deform or move the plurality of nodes on the first and second strands, and an uncharged state in which the stored energy has been released. The wound filler transitions from the charged state to the uncharged state as the membrane softens in the presence of wound fluid. The transition is configured to dynamically change the position of the plurality of nodes against the wound site. The system further includes a drape positioned over the wound filler and capable of attaching to an intact portion of the patient's epidermis for creating a sealed space beneath the drape and a reduced pressure source for supplying reduced pressure to the sealed space.

In yet another embodiment, a system for treating a wound site on a patient with reduced pressure includes a wound filler. The wound filler includes a web having a plurality of nodes positioned on the web, and a removable membrane fitted around the web such that a shape of the plurality of nodes are visible. The membrane holds the web in a potential energy state that when released would deform or move the plurality of nodes. The web gradually transitions into a resting state as the membrane dissolves in the presence of wound fluid. The system further includes a drape positioned over the wound filler and capable of attaching to an intact portion of the patient's epidermis for creating a sealed space beneath the drape and a reduced pressure source for supplying reduced pressure to the sealed space.

Other objects, features, and advantages of the illustrative embodiments will become apparent with reference to the drawings and detailed description that follow.

DETAILED DESCRIPTION OF ILLUSTRATIVE EMBODIMENTS

In the following detailed description of several illustrative embodiments, reference is made to the accompanying drawings that form a part hereof, and in which is shown by way of illustration specific preferred embodiments in which the subject matter of this specification may be practiced. These embodiments are described in sufficient detail to enable those skilled in the art to practice the disclosed subject matter, and it is understood that other embodiments may be utilized and that logical, structural, mechanical, electrical, and chemical changes may be made without departing from the scope of this specification. To avoid detail not necessary to enable those skilled in the art to practice the embodiments described herein, the description may omit certain information known to those skilled in the art. The following detailed description is, therefore, not to be taken in a limiting sense, with the scope of the illustrative embodiments being defined only by the appended claims. Unless otherwise indicated, as used herein, "or" does not require mutual exclusivity.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

Typically, static wound fillers used in long duration applications, i.e., wound fillers used for three or more days, are at risk for tissue in-growth, whereby newly formed tissue grows into the wound filler. When the wound filler is later removed, there is the risk that some of the newly formed tissue will be removed with the wound filler, or portions of the wound filler will remain at the tissue site Additionally, static wound fillers used in long duration applications may expose portions of the tissue site to microstrains for too long a period of time When portions of the tissue site are exposed to microstrains for too long a period of time, the higher stress areas may not be able to form new granulation tissue. The result may be a wound bed with a mixture of very high granulation zones and zones of no granulation formation.

The tissue treatment systems and apparatuses described herein can improve the treatment of a tissue site by providing a wound filler having dynamic motion that is used in conjunction with reduced pressure treatment. The wound filler includes a plurality of nodes that expose the tissue site to micro-mechanical stresses and strains. The wound filler has a first, charged state, in which the wound filler stores energy in the form of potential energy that when released moves the plurality of nodes. The wound filler also has a second, resting state, in which the stored energy has been released. The wound filler gradually transitions from the first state to the second state. As the wound filler transitions, the plurality of nodes move across the wound site creating microstrain at the tissue site. The plurality of nodes transmit a force to the tissue site where the nodes contact the tissue site. This force may be referred to as a point load. The force distribution of the plurality of nodes across the tissue site results in a particular microstrain distribution, which varies based on the force distribution and the rate at which the wound filler transitions between the first state and the second state. Since microstrain at the tissue site assists in the development of new granulation tissue, it is beneficial to vary the distribution of force and microstrain during treatment such that a more even development of granulation tissue is obtained.

Figure 1:
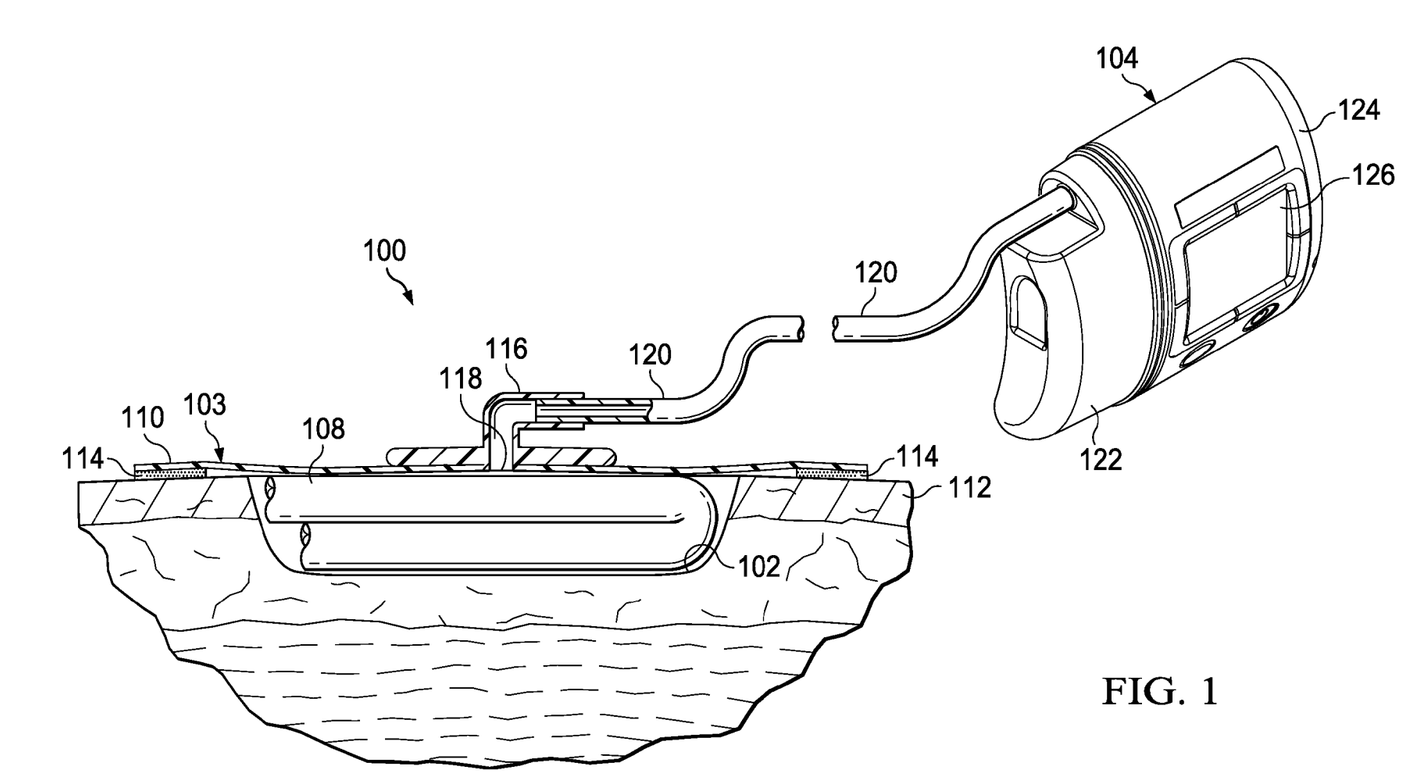
FIG. 1 illustrates a perspective view, with a portion shown in cross-section, of a reduced pressure treatment system, including a wound filler according to an illustrative embodiment.

Referring to FIG. 1, an illustrative embodiment of a tissue treatment system 100 for treating a tissue site 102 on a patient includes a dressing 103 placed proximate to the tissue site 102 and a therapy unit 104 fluidly coupled to the dressing 103. As used herein, the term "tissue site" may refer to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

The dressing 103 is configured to promote growth of new tissue at the tissue site 102 and includes a wound filler 108 positioned adjacent to, or in some embodiments, in contact with, the tissue site 102. The dressing 103 may further include a cover or drape 110 positioned over the wound filler 108 to secure the wound filler 108 at the tissue site 102 and to seal a space that is located beneath the cover and that is at least partially occupied by the wound filler 108. The drape 110 contains the wound filler 108 at the tissue site 102 as the wound filler 108 transitions from the charged state to the resting state. In one embodiment, the drape 110 extends beyond a perimeter of the tissue site 102 and is placed either in contact with or otherwise in proximity to a patient's epidermis 112 to create a fluid seal between the drape 110 and the epidermis 112. The drape 110 may include an adhesive 114 or bonding agent to secure the drape 110 to the epidermis 112. In one embodiment, the adhesive 114 may be used to create a seal between the drape 110 and the epidermis 112 to prevent leakage of reduced pressure from the tissue site 102. In another embodiment, a seal layer (not shown) such as, for example, a hydrogel or other material may be disposed between the drape 110 and the epidermis 112 to augment or substitute for the sealing properties of the adhesive 114. As used herein, "fluid seal" means a seal adequate to maintain reduced pressure at a desired site given the particular reduced pressure source involved and the particular treatment desired. In one embodiment, the drape 110 and the bonding characteristics of the drape 110 provide sealing sufficient to prevent leakage greater than 0.5 L/min at 125 mmHg reduced pressure.

The dressing 103 may further include a reduced pressure interface 116 in fluid communication with the space beneath the drape 110. In one embodiment, the interface 116 may be positioned adjacent to or coupled to the drape 110 to provide fluid access to the wound filler 108 and the tissue site 102. The drape 110 includes an aperture 118 for providing fluid access to the interface 116. A conduit 120 fluidly couples the therapy unit 104 and the interface 116. The interface 116 is capable of delivering reduced pressure to the tissue site 102.

In one embodiment, the therapy unit 104 includes a fluid containment member 122 in fluid communication with a reduced pressure source 124. In the embodiment illustrated in FIG. 1, the fluid containment member 122 is a collection canister that includes a chamber for collecting fluids from the tissue site 102. The fluid containment member 122 alternatively could be an absorbent material or any other container, device, or material that is capable of collecting fluid.

The conduit 120 may be a multi-lumen tube having one or more conduits to deliver reduced pressure to the dressing 103 and one or more conduits to sense the amount of pressure at the tissue site 102. Liquids or exudates communicated from the wound filler 108 through the conduit 120 are removed from the conduit 120 and retained within the fluid containment member 122.

Referring still to FIG. 1, the reduced pressure source 124 may be an electrically driven vacuum pump. In another implementation, the reduced pressure source 124 instead may be a manually-actuated or manually-charged pump that does not require electrical power. In one embodiment, the reduced pressure source 124 may be one or more piezoelectric-actuated micropumps that may be positioned remotely from the dressing 103, or at the dressing beneath or adjacent to the drape 110. The reduced pressure source 124 instead may be any other type of pump, or alternatively, a wall suction port or air delivery port such as those available in hospitals and other medical facilities. The reduced pressure source 124 may be housed within or used in conjunction with the therapy unit 104, which may also contain sensors, processing units, alarm indicators, memory, databases, software, display units, and user interfaces 126 that further facilitate the application of reduced pressure treatment to the tissue site 102. In one example, pressure-detection sensors (not shown) may be disposed at or near the reduced pressure source 124. The pressure-detection sensors may receive pressure data from the interface 116 via lumens in the conduit 120 that are dedicated to delivering reduced pressure data to the pressure-detection sensors. The pressure-detection sensors may communicate with a processing unit that monitors and controls the reduced pressure that is delivered by the reduced pressure source 124.

Figure 2:
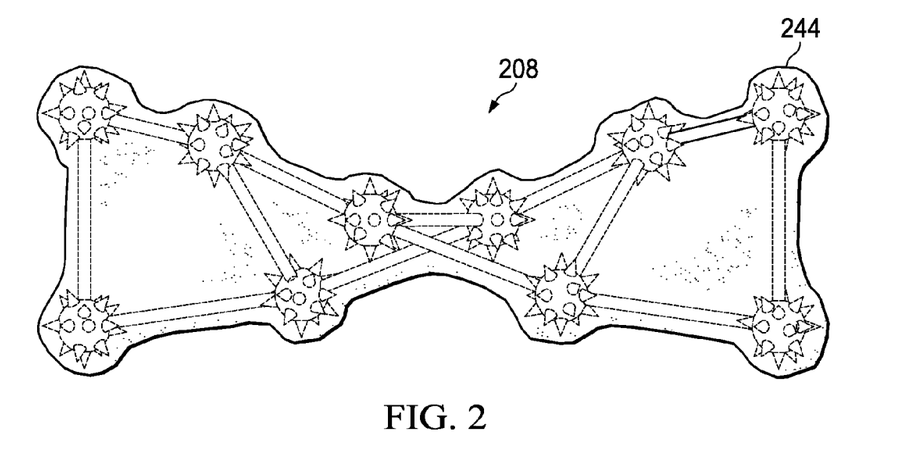
FIG. 2 illustrates an embodiment of a wound filler in a first, charged state, having a sheath and an interior portion shown with hidden lines, for use with the reduced pressure treatment system illustrated in FIG. 1.
Figure 3A:
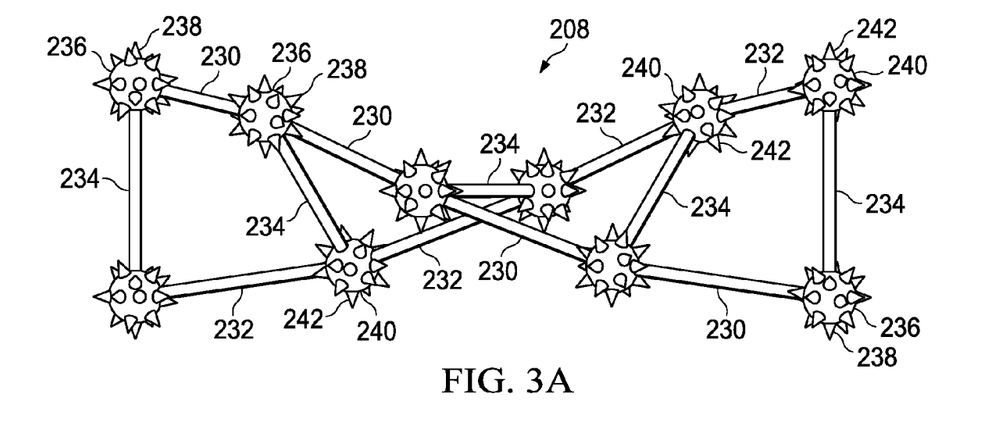
FIG. 3A illustrates the wound filler of FIG. 2 without the sheath in the first, charged state.
Figure 3B:
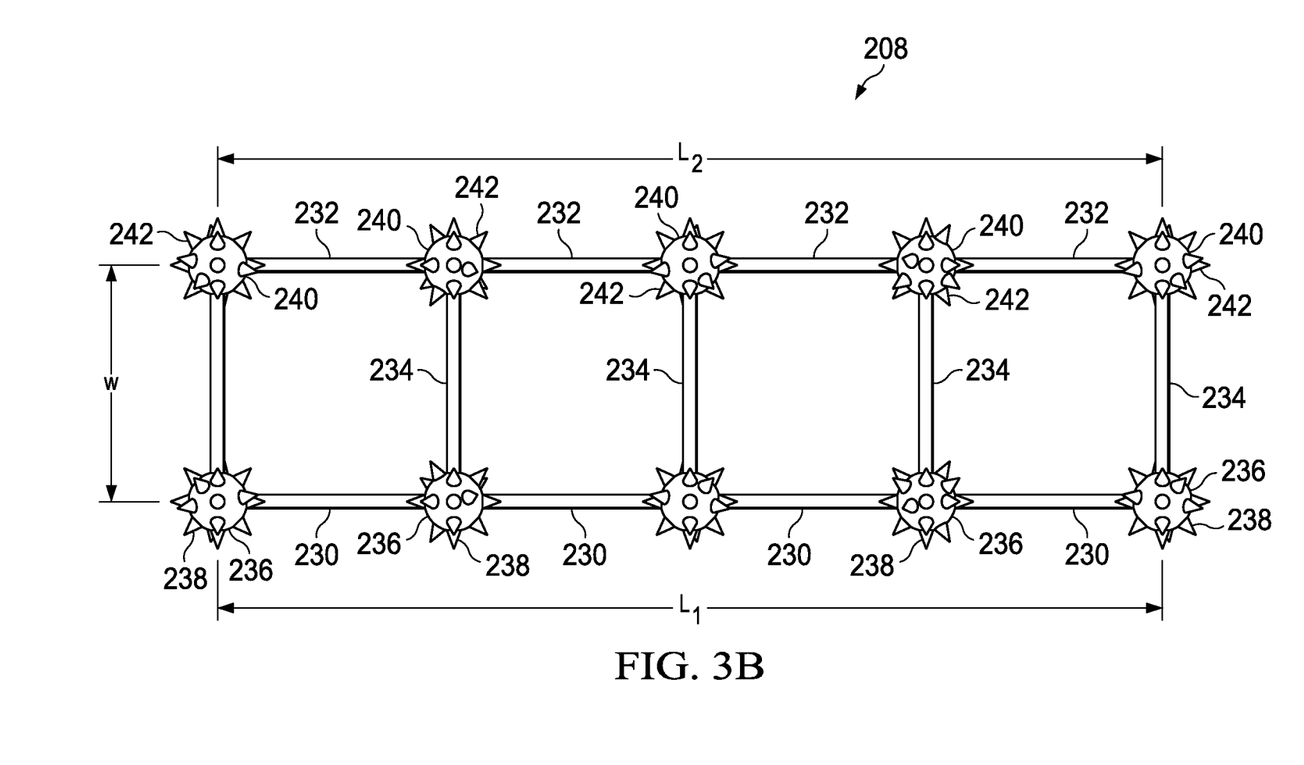
FIG. 3B illustrates the wound filler of FIG. 2 without the sheath in the second, uncharged state.

Referring now primarily to FIGS. 2, 3A and 3B, an illustrative embodiment of a wound filler 208 for use in the system 100 of FIG. 1 is presented. The wound filler 208 is positioned adjacent to, or in some embodiments, in contact with, the tissue site 102. The wound filler 208 creates point loads at the tissue site 102 where the wound filler 208 contacts the tissue site 102. These point loads cause micro-mechanical stresses and strains at the tissue site 102. The wound filler 208 is configured to move against and relative to the tissue site 102. The wound filler 208 has a first, or charged, state in which the wound filler 208 includes a stored energy that when released deforms or moves the wound filler 208. The stored energy may be in the form of potential energy. The wound filler 208 also has a second, or discharged, state in which the stored energy has been released and the wound filler 208 is at rest. FIG. 3A shows one embodiment of the wound filler 208 in the charged state, and FIG. 3B shows the wound filler 208 in the uncharged state. The energy stored in the wound filler 208 enables the wound filler 208 to move against the tissue site 102 during therapy without the need for an external energy source or interaction. The wound filler 208 is configured to transition from the charged state to the discharged state irrespective of reduced pressure acting on the wound filler 208. The wound filler 208 is further configured to allow for fluid flow to and from the tissue site 102 while manifolding or distributing the reduced pressure to the tissue site 102. The mechanisms for transitioning the wound filler 208 from the charged state to the discharged state will be discussed in more detail below.

The transition of the wound filler 208 from the charged state to the discharged state causes the wound filler 208 to move against and relative to the tissue site 102. As the wound filler 208 moves against the tissue site 102, portions of the tissue site 102 exposed to the movement path of the wound filler 208 are exposed to micro-mechanical stresses and strains, thereby creating a particular micro-strain distribution across the tissue site 102. The micro-mechanical stresses and strains at the tissue site 102 assist in the development of new granulation tissue. Thus, moving the location of the point loads, the point loads being caused by the wound filler 208, creates a more even distribution of new granulation tissue than static wound fillers for at least two reasons. First, dynamically moving the location of the point loads exposes a greater area of the tissue site to micro-mechanical stresses and strains. Second, leaving a wound filler that is exerting a point load against a tissue site in one place for too long may actually prevent or inhibit the growth of new tissue in the area of tissue site under the point load. Leaving the point load against a tissue site for too long may prevent the growth of new granulation tissue at the tissue site surrounding the point load creating areas in the tissue site having high granulation formation and areas having low granulation formation. Thus, the tissue site might experience uneven granulation formation.

The wound filler 208 includes a first strand 230 and a second strand 232. While the wound filler 208 is shown as having the first strand 230 and the second strand 232, it should be appreciated that the wound filler 208 may only have one strand, or the wound filler 208 may include a plurality of strands. The first strand 230 is connected to the second strand 232 by a plurality of struts or rods 234. The first and second strands 230, 232 as well as the plurality of rods 234 may be formed from a woven or non-woven material or fabric. In one embodiment, the first and second strands 230, 232 and the plurality of rods 234 may be comprised of fibers. The first and second strands 230, 232 and the plurality of rods 234 may also be formed from a number of different materials, including polymers such as polyester, polyamide, polyethylene, polyurethane, and thermoplastic elastomers. Further, the first and the second strands 230, 232 and the plurality of rods 234 may be formed of silicone, or metals such as stainless steel. The first and the second strands 230, 232 and the plurality of rods 234 may be made from only polymers, only metals, or a combination of polymers and metals. The material or material combination may be varied to provide a range of hard to soft options.

The material used to form at least the first strand 230, the second strand 232, and the plurality of rods 234 is resilient so that when the first strand 230, the second strand 232, and the plurality of rods 234 are twisted or deformed, the first strand 230, the second strand 232, and the plurality of rods 234 will return to their resting state without permanent deformation. When the first strand 230, the second strand 232, and the plurality of rods 234 are twisted or deformed, potential energy is created within the first strand 230, the second strand 232, and the plurality of rods 234. In other words, when the first strand 230, the second strand 232, and the plurality of rods 234 are deformed, internal forces act to restore the first strand 230, the second strand 232, and the plurality of rods 234 to their resting state. The first strand 230, the second strand 232, and the plurality of rods 234 may be twisted or deformed from their resting state when they are adjacent the tissue site 102 by patient movement, flexing at the tissue site 102, forces from the drape, and the periodic release of the reduced pressure at the tissue site 102. In one embodiment, the first strand 230, the second strand 232, and the plurality of rods 234 are positioned adjacent the tissue site 102 in the charged state. Over a certain time period, the first strand 230, the second strand 232, and the plurality of rods 234 transition into the uncharged state. Patient movement, flexing at the tissue site 102, forces from the drape, and the periodic release of the reduced pressure at the tissue may twist or deform the first strand 230, the second strand 232, and the plurality of rods 234, creating internal forces within the first strand 230, the second strand 232, and the plurality of rods 234. The internal forces act to restore the first strand 230, the second strand 232, and the plurality of rods 234 to their resting state.

As depicted in FIG. 2, the wound filler 208 may further include a membrane or sheath 244 that surrounds, covers, or encases the first strand 230, the second strand 232, and the plurality of rods 234. The first strand 230, the second strand 232, and the plurality of rods 234 may be held in the charged state by the membrane or sheath 244. The membrane or sheath 244 may be a coating applied to the first strand 230, the second strand 232, and the plurality of rods 234. For ease of explanation, the first strand 230, the second strand 232, and the plurality of rods 234 may sometimes be referred to as the inner portion of the wound filler 208 whereas the sheath 244 or coating may be referred to as the outer portion of the wound filler 208. The sheath 244 may hold or help hold the first and second strands 230, 232 and the plurality of rods 234 in the charged state. In one embodiment, the sheath 244 is configured to be removed from the first strand 230, the second strand 232, and the plurality of rods 234. Removal of the sheath 244 causes the wound filler 208 to transition from the first, charged state to the second, uncharged state. The sheath 244 may be physically removed by a healthcare provider.

In another embodiment, the sheath 244 may be formed from a water soluble cover, or a water soluble coating. The water soluble cover and the water soluble coating may be formed from a polyvinyl alcohol and its copolymers, carboxyl and hydroxyl substituted acrylics and salts, polyethylene glycols, polyvinyl pyrrolidones, carboxymethycellulose and its salts, and sugars. In another embodiment, the sheath is bioabsorbable and dissolves in the presence of fluid such as a wound fluid. The material used to form the sheath 244 may be chosen based on the rate to dissolution of the material. The rate to dissolution may be from less than one hour up to several days. In one specific, non-limiting example, the rate to dissolution may be 1 hour, 3 hours, 12 hours, 24 hours, 2 days, 3 days, or more. As the sheath 244 dissolves, the ability of the sheath 244 to hold the first strand 230, the second strand 232, and the plurality of rods 234 in the charged state weakens. Thus, as the sheath 244 dissolves, the first strand 230, the second strand 232, and the plurality of rods 234 may gradually transition from the charged state to the uncharged state over a period of time as the potential energy stored in the first strand 230, the second strand 232, and the plurality of rods 234 is released. The time period over which the first strand 230, the second strand 232, and the plurality of rods 234 transition from the charged state to the uncharged state depends on the material properties of the chosen sheath 244, e.g., the material's rate to dissolution. As the sheath 244 dissolves and weakens, the internal forces acting on the first strand 230, the second strand 232, and the plurality of rods 234, i.e., the forces acting to release the stored potential energy and return to the resting state, begin to overcome the force of the sheath 244, i.e., the force acting on the first strand 230, the second strand 232, and the plurality of rods 234 to stay in the charged state.

In another embodiment, the sheath 244 may soften but not dissolve in the presence of fluid. In this embodiment, the softening of the sheath 244 allows the internal forces of the first strand 230, the second strand 232, and the plurality of rods 234 to overcome the force of the sheath holding the first strand 230, the second strand 232, and the plurality of rods 234 in the first, charged state. As the internal forces of the first strand 230, the second strand 232, and the plurality of rods 234 overcome the force of the sheath 244, the first strand 230, the second strand 232, and the plurality of rods 234 transition from the first, charged state to the second, uncharged state. The rate of transition from the charged state to the uncharged state may at least partially depend on how soft the sheath 244 becomes in the presence of fluid and the internal forces acting on the first strand 230, the second strand 232, and the plurality of rods 234.

The first strand 230 includes a plurality of nodes 236 positioned along a length, L1, of the first strand 230. The plurality of nodes 236 expose the tissue site 102 to micro-mechanical stresses and strains. The plurality of nodes 236 transmit a force to the tissue site 102 where the plurality of nodes 236 contact the tissue site 102. The force may be referred to as a point load. The plurality of nodes 236 may be spaced apart in equal distances along the length, L1, of the first strand 230. In one embodiment, the plurality of nodes 236 may be spaced apart along the length, L1, of the first strand 230 at random distances relative to each other. In yet another embodiment, the plurality of nodes 236 may be spaced apart from each other along the length, L1, of the first strand 230 in a repeating pattern.

The plurality of nodes 236 may be formed in a plurality of shapes. The plurality of nodes 236 are shown as having a circular or spherical shape. However, the plurality of nodes 236 may be pyramidal, oblong, square, or any number of shapes that allow the plurality of nodes 236 to transmit the desired point load to the tissue site 102 conducive to promoting new tissue granulation. The shape of each of the plurality of nodes 236 may be uniform, or the shape of each of the plurality of nodes 236 may be different. For example, one of the plurality of nodes 236 on the first strand 230 may be circular and another of the plurality of nodes 236 on the first strand 230 may be pyramidal.

The plurality of nodes 236 located on the first strand 230 may include a plurality of surface features or protrusions 238 extending from the plurality of nodes 236. The plurality of protrusions 238 may aid the plurality of nodes 236 in creating micro-mechanical stresses and strains at the tissue site 102. The plurality of protrusions 238 are shown as having a spike shape. However, the plurality of protrusions 238 may be formed in a number of shapes. For example, the plurality of protrusions 238 may be cylindrical, pyramidal, or a number of shapes that aid the plurality of nodes 236 in transmitting the desired point load to the tissue site 102 conducive to promoting new tissue granulation. The shape of each of the plurality of protrusions 238 may be uniform, or the shape of each of the plurality of protrusions 238 may be different. In one embodiment, the plurality of protrusions 238 on each of the plurality of nodes 236 is uniform. In another embodiment, the shape of the plurality of protrusions 238 on one of the plurality of nodes 236 is different than the shape of the plurality of protrusions 238 on another of the plurality of nodes 236. In yet another embodiment, the plurality of protrusions 238 on one of the plurality of nodes 236 may take a number of different shapes. For example, one of the plurality of protrusions 238 on the plurality of nodes 236 may be circular and another of the plurality of protrusions 238 on the plurality of nodes 236 may be pyramidal.

The plurality of nodes 236 may have a diameter of approximately 0.5 millimeters (mm) to approximate the pore size (strut spacing) of an open-celled foam such as the open-celled, reticulated polyurethane foam sold under the name GRANUFOAM® by Kinetic Concepts, Inc. of San Antonio, Tex. The pore size of GRANUFOAM® has been modeled by finite element analysis (FEA) to be in the range of 0.3 mm to 1 mm. The pitch or spacing of the plurality of nodes 236 may be greater than or equal to two times the node size. In a non-limiting example, the spacing of the nodes 236 may be 1 mm to 3 mm. The spacing between the nodes 236 may be adjusted based on the size of the protrusions 238 extending from the nodes 236. The protrusions 238 may extend from the nodes 236, in a specific, non-limiting example, from 0.1 mm up to 0.5 mm. In the instance where the protrusions 238 extend from the nodes 236 up to 0.5 mm, which may consequently be the size of the nodes 236, a polyhedron may be formed rather than a sphere. The length, L1, of the first strand 230 may be manufactured as a number of sizes. In one embodiment, the length, L1, is approximately 1 meter (m). The length, L1, may be sized depending on the size of the tissue site 102.

The second strand 232 also includes a plurality of nodes 240 positioned along a length, L2, of the second strand 232. The plurality of nodes 240 expose the tissue site 102 to micro-mechanical stresses and strains. The plurality of nodes 240 transmit a force to the tissue site 102 where the plurality of nodes 240 contact the tissue site 102. The force may be referred to as a point load. The plurality of nodes 240 may be spaced apart in equal distances along the length, L2, of the second strand 232. In one embodiment, the plurality of nodes 240 may be spaced apart along the length, L2, of the second strand 232 at random distances relative to each other. In yet another embodiment, the plurality of nodes 240 may be spaced apart from each other along the length, L2, of the second strand 232 in a repeating pattern.

The plurality of nodes 240 may be formed in a plurality of shapes. The plurality of nodes 240 are shown as having a circular or spherical shape. However, the plurality of nodes 240 may be pyramidal, oblong, square, or any number of shapes that allow the plurality of nodes 240 to transmit the desired point load to the tissue site 102 conducive to promoting new tissue formation. The shape of each of the plurality of nodes 240 may be uniform, or the shape of each of the plurality of nodes 240 may be different. For example, one of the plurality of nodes 240 on the second strand 232 may be circular and another of the plurality of nodes 240 on the second strand 232 may be pyramidal.

The plurality of nodes 240 located on the second strand 232 may include a plurality of surface features or protrusions 242 extending from the plurality of nodes 240. The plurality of protrusions 242 may aid the plurality of nodes 240 in creating micro-mechanical stresses and strains at the tissue site 102. The plurality of protrusions 242 are shown as having a spike shape. However, the plurality of protrusions 242 may be formed in a number of shapes. For example, the plurality of protrusions 242 may be cylindrical, pyramidal, or a number of shapes that aid the plurality of nodes 240 in transmitting the desired point load to the tissue site 102 conducive to promoting new tissue granulation. The shape of each of the plurality of protrusions 242 may be uniform, or the shape of each of the plurality of protrusions 242 may be different. In one embodiment, the plurality of protrusions 242 on each of the plurality of nodes 240 is uniform. In another embodiment, the shape of the plurality of protrusions 242 on one of the plurality of nodes 240 is different than the shape of the plurality of protrusions 242 on another of the plurality of nodes 240. In yet another embodiment, the plurality of protrusions 242 on one of the plurality of nodes 240 may take a number of different shapes. For example, one of the plurality of protrusions 242 on the plurality of nodes 240 may be circular and another of the plurality of protrusions 242 on the plurality of nodes 240 may be pyramidal.

The plurality of nodes 240 may have a diameter of approximately 0.5 millimeters (mm) to approximate the pore size (strut spacing) of an open-celled foam such as the open-celled, reticulated polyurethane foam sold under the name GRANUFOAM® by Kinetic Concepts, Inc. of San Antonio, Tex. The pore size of GRANUFOAM® has been modeled by finite element analysis (FEA) to be in the range of 0.3 mm to 1 mm. The pitch or spacing of the plurality of nodes 240 may be greater than or equal to two times the node size. In a non-limiting example, the spacing of the nodes 240 may be 1 mm to 3 mm. The spacing between the nodes 240 may be adjusted based on the size of the protrusions 242 extending from the nodes 240. The protrusions 242 may extend from the nodes 240 in a specific, non-limiting example, from 0.1 mm up to 0.5 mm. In the instance where the protrusions 242 extend from the nodes 240 up to 0.5 mm, which may consequently be the size of the nodes 240, a polyhedron may be formed rather than a sphere. The length, L2, of the second strand 232 may be manufactured as a number of sizes. In one embodiment, the length, L2, is approximately 1 meter (m). The length, L2, may be sized depending on the size of the tissue site 102.

In one embodiment, the first strand 230, including the plurality of nodes 236 and the plurality of protrusions 238, may be identical to the second strand 232, including the plurality of nodes 240 and the plurality of protrusions 242. As previously mentioned, the first strand 230 is connected to the second strand 232 by the plurality of rods or struts 234. In one embodiment, the plurality of rods 234 connect the first strand 230 to the second strand 232 by connecting the plurality of nodes 236 on the first strand 230 to the plurality of nodes 240 on the second strand 232. The width, W, of the plurality of rods 234 extending between the first and second strands 230, 232 may be greater than or equal to the size of the nodes 236, 240. In one specific, non-limiting embodiment, the width, W, is 1.5 mm to 5 mm. The plurality of rods 234 may connect the first strand 230 to the second strand 232 to form a ladder configuration. In one embodiment, a plurality of protrusions (not shown) may extend from the plurality of rods 234.

The sheath 244 that surrounds the first strand 230, the second strand 232 and the plurality of rods 234 also surrounds the plurality of nodes 236, 240 and the plurality of protrusions 238, 242 extending, respectively, from the plurality of nodes 236, 240. The plurality of nodes 236, 240 and the plurality of protrusions 238, 242 may be visible underneath the sheath 244. In one embodiment, the sheath 244 is form fitted around the inner portion of the wound filler 208, the inner portion including the first strand 230, the second strand 232, the plurality of rods 234, the plurality of nodes 236, 240, and the plurality of protrusions 238, 242. The sheath 244 is form fitted around the inner portion allowing the shape of the inner portion to be visible. The sheath 244 may be form fitted around the inner portion by heat shrinking the sheath 244 around the inner portion. In another embodiment, the first strand 230, the second strand 232, the plurality of rods 234, the plurality of nodes 236, 240, and the plurality of protrusions 238, 242 are coated with the sheath 244. The sheath 244 may be coated onto the inner portion by dipping the inner portion into sheath material. Alternatively, the sheath 244 may be coated onto the inner portion by spraying the inner portion with sheath material.

In operation, in one embodiment, the wound filler 208 in the charged state is positioned adjacent the tissue site 102. The wound filler 208 may be sized by the healthcare provider to fit the tissue site 102 prior to positioning the wound filler adjacent the tissue site 102. In the event the tissue site 102 is a surface wound, a healthcare provider may place the wound filler 208 directly adjacent the tissue site 102. In the event the tissue site 102 is subcutaneous, the wound filler 208 may be positioned adjacent to the tissue site 102 by feeding the wound filler 208 through an access port or other tubing that extends from the subcutaneous tissue site 102 to an exterior portion of the patient. In one embodiment, the wound filler 208 may be placed adjacent the subcutaneous tissue site 102 after the drape 110 and the reduced pressure interface 116 have been positioned. Once the wound filler 208 has been secured at the tissue site 102 and the therapy unit 104 has been connected, reduced pressure is applied to the tissue site 102. The wound filler 208 begins to transition from the charged state to the uncharged state. In one embodiment, the wound filler 208 transitions due to the sheath 244 softening or dissolving. In another embodiment, the wound filler transitions due to the sheath 244 being removed.

In operation, a direct pressure control mode on the therapy unit 104 may be used to reduce the reduced pressure, i.e., increase the absolute pressure, on the wound filler 208 during therapy to allow the nodes 236, 240 to reposition as the drape 110 tension reduces during the pressure change and as the tissue site 102 changes shape during patient motion. Thus, the amount of potential energy stored in the wound filler 208 required to achieve the therapeutic effects can be reduced and controlled by controlling the reduced pressure utilizing, for example, the direct pressure control mode on the therapy unit 104.

Figure 4A:
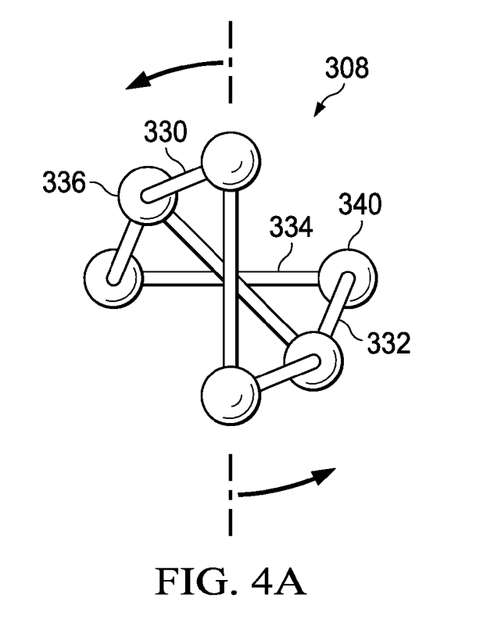
FIG. 4A illustrates another embodiment of a wound filler in a first state.

Referring now primarily to FIGS. 4A-6, another illustrative embodiment of a wound filler 308 for use in the system 100 of FIG. 1 is presented. The wound filler 308 is similar to the wound filler 208 of FIGS. 2-3B except the wound filler 308 may form a double helix in both the charged state and the uncharged state. The wound filler 308 is positioned adjacent to, or in some embodiments, in contact with, the tissue site 102. The wound filler 308 has a first, or charged state in which the wound filler 308 includes a stored energy that when released deforms or moves the wound filler 308. The wound filler 308 also has a second, or discharged state in which the stored energy has been released and the wound filler 308 is at rest. In one embodiment, FIG. 4A shows the wound filler 308 in the charged state, and FIG. 4B shows the wound filler 308 in the uncharged state. The energy stored in the wound filler 308 enables the wound filler 308 to move against the tissue site 102 during therapy without the need for an external energy source or interaction.

Figure 4B:
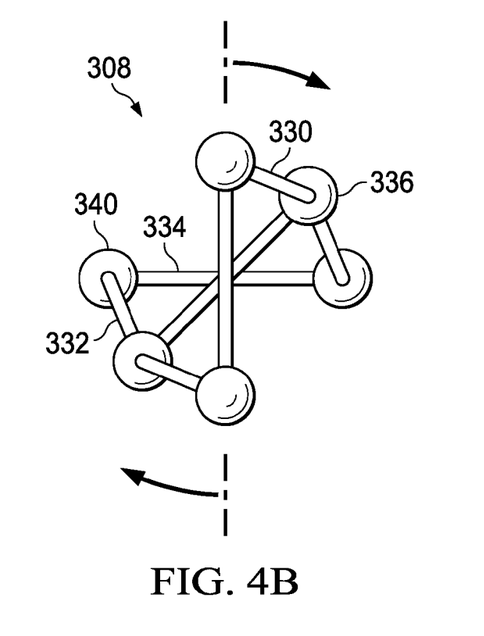
FIG. 4B illustrates the wound filler of FIG. 4A in a second state.

The wound filler 308 includes a first strand 330 and a second strand 332. The first strand 330 is connected to the second strand 332 by a plurality of rods or struts 334. The first and second strands 330, 332 and the plurality of rods 334 may be formed from a number of different materials, including polymers such as polyester, polyamide, polyethylene, polyurethane, and thermoplastic elastomers. The first and second strands 330, 332 and the plurality of rods 334 may also be formed of silicone, and metals such as stainless steel. Further, the first and second strands 330, 332 and the plurality of rods 334 may be made from only polymers, only metals, or a combination of polymers and metals. The material or material combination may be varied to provide a range of hard to soft options.

The first and second strands 330, 332 include a first and second plurality of nodes 336, 340, respectively, positioned along a length of the first and the second strands 330, 332. The plurality of nodes 336, 340 may be formed in a plurality of shapes. The plurality of nodes 336, 340 may include a plurality of surface features or protrusions (not shown) extending from the plurality of nodes 336, 340. The plurality of protrusions may aid the plurality of nodes 336 and 340 in creating micro-mechanical stresses and strains at the tissue site 102.

Figure 5:
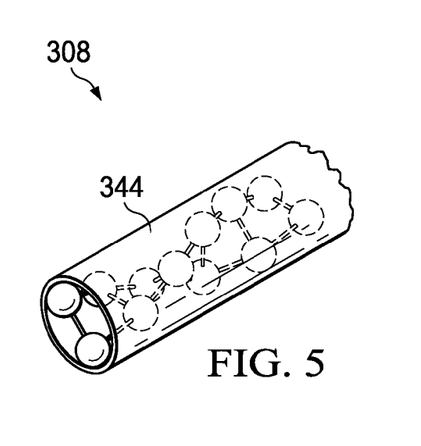
FIG. 5 illustrates an embodiment of the wound filler of FIGS. 4A and 4B having a sheath for use with the reduced pressure treatment system illustrated in FIG. 1.
Figure 6:
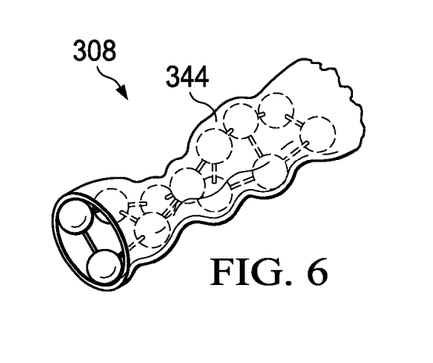
FIG. 6 illustrates another embodiment of the wound filler of FIGS. 4A and 4B having a sheath for use with the reduced pressure treatment system illustrated in FIG. 1.

As depicted in FIGS. 5 and 6, the wound filler 308 further includes a membrane or sheath 344 that surrounds, covers, or encases an inner portion of the wound filler 308, including the first strand 330, the second strand 332, the plurality of rods 334, and the plurality of nodes 336, 340. The inner portion of the wound filler 308 may be held in the charged state by the membrane or sheath 344. In one embodiment, the membrane or sheath 344 may be a coating applied to the inner portion of the wound filler 308. In another embodiment illustrated in FIG. 5, the sheath 344 surrounds the inner portion of the wound filler 308 holding the inner portion in an initially charged state. In another embodiment illustrated in FIG. 6, the sheath 344 also surrounds the inner portion of the wound filler 308, holding the inner portion in an initially charged state, but the sheath 344 has been heat shrinked over the inner portion.

Figure 7:
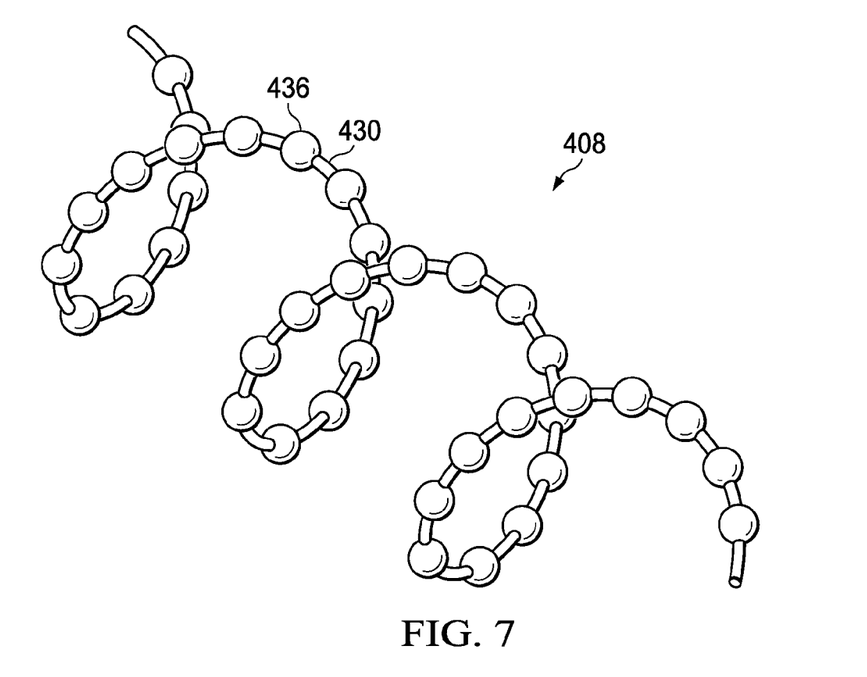
FIG. 7 illustrates another embodiment of a wound filler for use with the reduced pressure treatment system illustrated in FIG. 1.

Referring now primarily to FIG. 7, another illustrative embodiment of a wound filler 408 for use in the system 100 of FIG. 1 is presented. The wound filler 408 includes a strand or string 430 and a plurality of nodes 436. The plurality of nodes 436 may include a plurality of protrusions (not shown). The wound filler 408 may have a coiled configuration in either a charged or an uncharged state. Similar to the previously described embodiments, a coating may be applied to the wound filler 408 to hold the wound filler 408 in the charged state. Also similar to the previously described embodiments, the wound filler 408 may transition from the charged state to the uncharged state while positioned adjacent the tissue site 102 to create a path of micro-mechanical stresses and strains at the tissue site 102 to induce tissue granulation.

Figure 8:
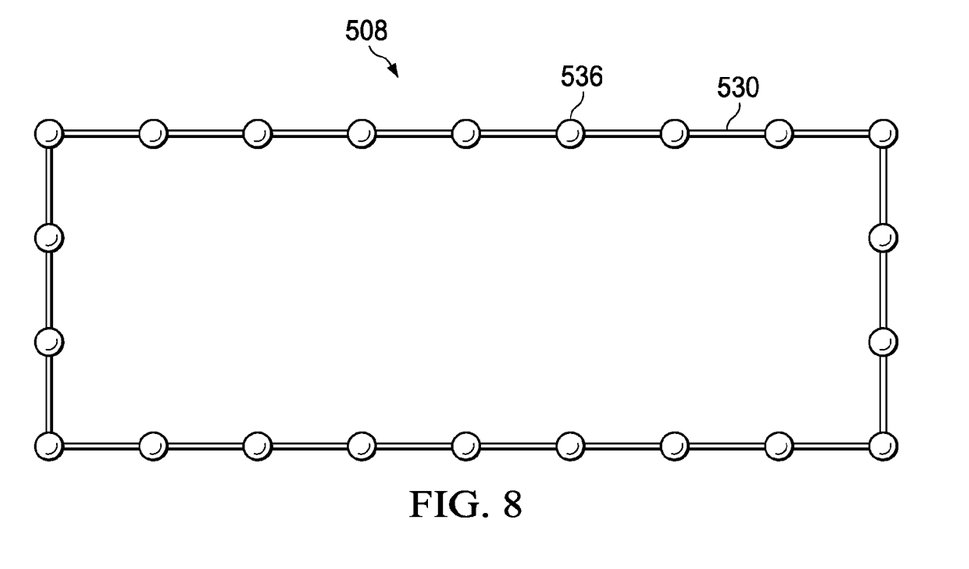
FIG. 8 illustrates another embodiment of a wound filler for use with the reduced pressure treatment system illustrated in FIG. 1.

Referring now primarily to FIG. 8, another illustrative embodiment of a wound filler 508 for use in the system 100 of FIG. 1 is presented. The wound filler 508 includes a ribbon 530 and a plurality of nodes 536 positioned on the ribbon 530. The plurality of nodes 536 may be positioned along the perimeter of the ribbon 530, or the plurality of nodes 536 may be placed along the perimeter and surface of the ribbon 530. The plurality of nodes 536 may include a plurality of protrusions (not shown). Similar to the previously described embodiments, a coating may be applied to the wound filler 508 to hold the wound filler 508 in the charged state. In one embodiment depicted in FIG. 8, the wound filler 508 is flat in the charged state. In another embodiment (not shown), the wound filler 508 is folded in the charged state. Similar to the other wound filler embodiments described, the wound filler 508 may transition from the charged state to the uncharged state while positioned adjacent the tissue site 102 to create a path of micro-mechanical stresses and strains at the tissue site 102 to induce tissue granulation.

In one embodiment (not shown), a plurality of nodes, having a plurality of protrusions extending from each of the plurality of nodes, may be connected to one another by a web or mesh. The web or mesh may be formed by weaving, knitting, or braiding. The plurality of nodes may be formed on filaments that are used to make the web or mesh. In another embodiment, the web or mesh may be formed by extrusion. The web, the plurality of nodes, and the plurality of protrusions may be formed from a number of different materials, including polymers such as polyester, polyamide, polyethylene, polyurethane, and thermoplastic elastomers. The web, the plurality of nodes, and the plurality of protrusions may also be formed of silicone, and metals such as stainless steel. Further, the web, the plurality of nodes, and the plurality of protrusions may be made from only polymers, only metals, or a combination of polymers and metals. The material or material combination may be varied to provide a range of hard to soft options. The material is resilient so that if the web, the plurality of nodes, and the plurality of protrusions are deformed, internal forces within the web, the plurality of nodes, and the plurality of protrusions will act to restore them to their resting state. The web, the plurality of nodes, and the plurality of protrusions may be covered or surrounded by a sheath or a coating. The web, the plurality of nodes, and the plurality of protrusions may be deformed or twisted into a first, charged state and held in the charged state by the sheath or coating. The sheath or coating may be removable. In one embodiment, the sheath is dissolvable. As the sheath is removed, the potential energy stored within the web, the plurality of nodes, and the plurality of protrusions may be released causing the web, the plurality of nodes, and the plurality of protrusions to move to its resting or discharged state. In other words, the web, the plurality of nodes, and the plurality of protrusions move back to their undeformed state. The transition between the charged state and the discharged state causes microstrain at the tissue site 102 promoting the growth of new tissue.

A number of techniques for manufacturing the wound filler are available. Extrusion techniques may be used to form the wound filler as a single piece. Alternatively, extrusion techniques may be used to form filaments having nodes where the filaments are then woven, braided or knitted into the wound filler. Sequential injection molding may be used to form the wound filler. In one embodiment, the plurality of protrusions may be applied in a secondary step where the mesh or wound filler is coated with an adhesive and subsequently coated with particulates of the desired shape and size. The mesh or wound filler may be twisted or braided and then fed into an extruder where a coating is applied. Alternatively the twisted mesh or wound filler may be coated by a dipping process and then dried under tension.

In one embodiment, the wound fillers described above may include channels to facilitate fluid flow. In another embodiment, a polymer may be used to form portions of the wound fillers described above that is adapted to return to its charged state upon heat or light activation. For example, heat in the range of 40 degrees Centigrade to 45 degrees Centigrade may return the wound filler to the charged state.

While the subject matter of this specification is shown in only a few of its forms, the subject matter is not limited, but susceptible to various changes and modifications without departing from the scope thereof. Further, while a number of discrete embodiments have been described, aspects of each embodiment may be combined with features of other embodiments.

We claim:

1. A wound filler adapted to be positioned adjacent a tissue site for treating the tissue site, comprising:
at least one strand having a plurality of nodes positioned along a length of the strand, the at least one strand moveable from a charged state to a discharged state, wherein in the charged state the at least one strand includes a stored energy, and wherein the at least one strand is adapted to move from the charged state to the discharged state upon release of the stored energy; and
a removable sheath substantially encasing the at least one strand, the removable sheath adapted to retain the at least one strand in the charged state, wherein removal of the removable sheath permits the at least one strand to move to the discharged state.

2. The wound filler of claim 1, wherein at least one of the plurality of nodes has a circular shape.

3. The wound filler of claim 1, wherein at least one of the plurality of nodes has a pyramidal shape.

4. The wound filler of claim 1, wherein each of the plurality of nodes have a plurality of protrusions extending from each of the plurality of nodes.

5. The wound filler of claim 4, wherein the plurality of protrusions have a shape selected from the group consisting of a circular shape, a spiked shape, and a pyramidal shape.

6. The wound filler of claim 1, wherein the plurality of nodes are spaced apart in equal distances from one another along the length of the at least one strand.

7. The wound filler of claim 1, wherein the at least one strand is a first strand and a second strand, the first strand connected to the second strand by a plurality of rods.

8. The wound filler of claim 7, wherein in the charged state and in the discharged state, the first strand and the second strand form a double helix.

9. The wound filler of claim 7, wherein the first strand and the second strand are resilient, the first strand and the second strand being twisted and deformed in the charged state and untwisted and at rest in the discharged state.

10. The wound filler of claim 1, wherein the plurality of nodes each have a shape adapted to transmit a point load to the tissue site.

11. The wound filler of claim 1, wherein the removable sheath is bioabsorbable.

12. The wound filler of claim 11, wherein the at least one strand is adapted to gradually transition from the charged state to the discharged state upon dissolution of the bioabsorbable sheath.

13. The wound filler of claim 1, wherein the removable sheath is configured to dissolve in the presence of fluid from the tissue site.

14. The wound filler of claim 1, wherein the removable sheath is adapted to be removed in a time period that defines a rate of transition from the charged state to the discharged state.

15. The wound filler of claim 14, wherein the removable sheath is adapted to be gradually removed over a time period of 3 days.

16. The wound filler of claim 14, wherein the rate of transition defines the movement of the plurality of nodes.

17. The wound filler of claim 1, wherein the at least one strand is adapted to gradually transition from the charged state to the discharged state as the removable sheath is removed.

18. The wound filler of claim 1, wherein the at least one strand is resilient, the at least one strand being twisted and deformed in the charged state and untwisted and at rest in the discharged state.

19. The wound filler of claim 1, wherein the removable sheath is a coating.

20. A wound filler adapted to be positioned adjacent a tissue site for treating the tissue site, comprising:
a first strand having a plurality of nodes positioned along a length of the first strand;
a second strand having a plurality of nodes positioned along a length of the second strand, the first strand and the second strand moveable from a charged state to a discharged state, wherein in the charged state the first strand and the second strand include a stored energy, and wherein the first strand and the second strand are adapted to move from the charged state to the discharged state upon release of the stored energy;
at least one rod adapted to attach the first strand to the second strand; and
a removable sheath substantially surrounding both the first strand and the second strand, the removable sheath being dissolvable upon contact with fluid from the tissue site, wherein the first strand and the second strand are adapted to gradually transition from the charged state to the discharged state upon dissolution of the removable sheath, thereby providing movement relative to the tissue site of the plurality of nodes positioned along the first strand, the plurality of nodes positioned along the second strand, and the wound filler.

21. The wound filler of claim 20, wherein in the charged state and in the discharged state, the first strand and the second strand form a double helix shape.

22. The wound filler of claim 20, wherein each of the plurality of nodes on the first strand and the second strand have a plurality of protrusions extending from each of the plurality of nodes.

23. The wound filler of claim 20, wherein the removable sheath is bioabsorbable.

24. The wound filler of claim 20, wherein the removable sheath is adapted to be removed in a time period that defines a rate of transition from the charged state to the discharged state.

25. The wound filler of claim 24, wherein the removable sheath is adapted to be gradually removed over a time period of 3 days.

26. The wound filler of claim 24, wherein the rate of transition defines the movement of the plurality of nodes.

27. The wound filler of claim 20, wherein the first strand and the second strand are adapted to gradually transition from the charged state to the discharged state as the removable sheath is removed.

28. The wound filler of claim 20, wherein the first strand and the second strand are resilient, the first strand and the second strand being twisted and deformed in the charged state and the first strand and the second strand being untwisted and at rest in the discharged state.

29. A wound filler adapted to be positioned adjacent a tissue site for treating the tissue site, comprising:
a web having a plurality of nodes positioned on the web, the web being comprised of a resilient material and moveable from a charged state having stored energy to a discharged state upon release of the stored energy; and
a removable sheath fitted around the web and the plurality of nodes, the removable sheath substantially conforming to a shape defined by the web and the plurality of nodes, wherein the removable sheath is adapted to retain the web in the charged state and to dissolve upon contact with fluid from the tissue site, whereby dissolution of the removable sheath permits the web and the plurality of nodes to gradually transition from the charged state to the discharged state.

30. The wound filler of claim 29, wherein the web is a woven fabric comprised of fibers.

31. The wound filler of claim 29, wherein the web is a non-woven fabric comprised of fibers.

32. The wound filler of claim 29, wherein the plurality of nodes have a plurality of protrusions extending from each of the plurality of nodes.

33. The wound filler of claim 29, wherein the plurality of nodes are spaced apart in equal distances on the web.

34. The wound filler of claim 29, wherein the removable sheath is bioabsorbable.

35. The wound filler of claim 29, wherein the removable sheath is adapted to be removed in a time period that defines a rate of transition from the charged state to the discharged state.

36. The wound filler of claim 35, wherein the removable sheath is adapted to be gradually removed over a time period of 3 days.

37. The wound filler of claim 35, wherein the rate of transition defines the movement of the plurality of nodes.

38. The wound filler of claim 29, wherein the web is twisted and deformed in the charged state and untwisted and at rest in the discharged state.

39. The wound filler of claim 29, wherein the removable sheath is a coating.

40. A system for treating a tissue site with reduced pressure, comprising:
a wound filler adapted to be positioned adjacent the tissue site, comprising:
at least one strand having a plurality of nodes positioned along a length of the strand, the at least one strand moveable from a charged state to a discharged state, wherein in the charged state the at least one strand includes a stored energy, and wherein the at least one strand is adapted to move from the charged state to the discharged state upon release of the stored energy; and
a removable sheath substantially encasing the at least one strand, the removable sheath adapted to retain the at least one strand in the charged state, wherein removal of the removable sheath permits the at least one strand to move to the discharged state; and
a drape adapted to cover the wound filler at the tissue site to create a sealed space beneath the drape; and
a reduced pressure source adapted to supply reduced pressure to the sealed space.

* * * * *